(12) United States Patent
Molyneaux et al.

(10) Patent No.: US 11,393,559 B2
(45) Date of Patent: Jul. 19, 2022

(54) METHODS TO COMPRESS, ENCRYPT AND RETRIEVE GENOMIC ALIGNMENT DATA

(71) Applicant: SOPHIA GENETICS S.A., Saint Sulpice (CH)

(72) Inventors: Adam Molyneaux, Blonay (CH); Erman Ayday, Renens (CH); Jean-Pierre Hubaux, Saint-Sulpice (CH); Jesus Garcia, Saint Sulpice (CH); Zhicong Huang, Saint Sulpice (CH); Huang Lin, Saint Sulpice (CH)

(73) Assignee: SOPHIA GENETICS S.A., Saint Sulpice (CH)

( * ) Notice: Subject to any disclaimer, the term of this patent is extended or adjusted under 35 U.S.C. 154(b) by 175 days.

(21) Appl. No.: 16/083,325

(22) PCT Filed: Mar. 8, 2017

(86) PCT No.: PCT/EP2017/055414
§ 371 (c)(1),
(2) Date: Sep. 7, 2018

(87) PCT Pub. No.: WO2017/153456
PCT Pub. Date: Sep. 14, 2017

(65) Prior Publication Data
US 2019/0087601 A1 Mar. 21, 2019

(30) Foreign Application Priority Data
Mar. 9, 2016 (EP) .................................... 16159314

(51) Int. Cl.
*H04L 29/06* (2006.01)
*G16B 30/10* (2019.01)
(Continued)

(52) U.S. Cl.
CPC ............... *G16B 30/10* (2019.02); *G06F 7/78* (2013.01); *G06F 21/6227* (2013.01);
(Continued)

(58) Field of Classification Search
CPC ....... G06F 21/6227; G06F 7/78; G16B 20/00; G16B 30/00; H04L 9/0618
(Continued)

(56) References Cited

U.S. PATENT DOCUMENTS 10,354,748 B1 * 7/2019 Konerding ............. G16B 50/00
2014/0108323 A1 * 4/2014 Leighton ................ G06N 5/022
706/50
(Continued)

FOREIGN PATENT DOCUMENTS

CH 2816496 A1 * 12/2014
WO 2014/202615 12/2014

OTHER PUBLICATIONS

McKenna, "The Genome Analysis Toolkit: A MapReduce framework for analyzing next-generation DNA sequencing data", 2010, Cold Spring Harbor Laboratory Press, pp. 1297-1303 (Year: 2010).*
(Continued)

*Primary Examiner* — Taghi T Arani
*Assistant Examiner* — Gregory A Lane
(74) *Attorney, Agent, or Firm* — Bochner IP, PLLC; Andrew Bochner

(57) ABSTRACT

A genomic data decoder may jointly compress and encrypt genomic data alignment information while preserving the privacy of sensitive genomic data elements at retrieval stage. Genomic data alignment information organized as a read-based alignment data stream may be transposed into a position-based alignment data stream. The position-based alignment information may been coded into a reference-based alignment data stream. The reference-based alignment
(Continued)

data stream may be encrypted with a combination of order-preserving encryption of the genomic position information and symmetric encryption of the reference-based alignment differential data. Differential encoding and entropy coding schemes may further compress the reference-based alignment data stream. The resulting compressed and encrypted stream may be indexed and stored in a biobank storage unit. A genomic data decoder may efficiently retrieve, decrypt and decode a specific subset of the resulting compressed and encrypted stream without leaking information on the other genomic data subsets in the resulting stream.

20 Claims, 9 Drawing Sheets

(51) Int. Cl.
| | |
|---|---|
| *G16B 50/00* | (2019.01) |
| *G16B 30/00* | (2019.01) |
| *G16B 50/40* | (2019.01) |
| *G16B 50/50* | (2019.01) |
| *G16B 20/00* | (2019.01) |
| *G06F 7/78* | (2006.01) |
| *G06F 21/62* | (2013.01) |
| *H04L 9/06* | (2006.01) |

(52) U.S. Cl.
CPC ............ *G16B 20/00* (2019.02); *G16B 30/00* (2019.02); *G16B 50/00* (2019.02); *G16B 50/40* (2019.02); *G16B 50/50* (2019.02); *H04L 9/0618* (2013.01)

(58) Field of Classification Search
USPC ......................................................... 713/193
See application file for complete search history.

(56) References Cited

U.S. PATENT DOCUMENTS

| | | | |
|---|---|---|---|
| 2014/0200166 A1* | 7/2014 | Van Rooyen .......... | G16B 30/00 506/38 |
| 2015/0169824 A1* | 6/2015 | Kermani ................ | G16B 40/00 702/19 |
| 2016/0019339 A1* | 1/2016 | Sazonov ................ | G16B 30/00 702/20 |
| 2016/0080528 A1* | 3/2016 | Mishra .................. | G16B 30/00 713/168 |
| 2016/0259886 A1* | 9/2016 | Li .......................... | G16B 30/00 |
| 2016/0275308 A1 | 9/2016 | Hubaux | |
| 2017/0068776 A1* | 3/2017 | Godinez-Moreno .. | G16B 30/00 |

OTHER PUBLICATIONS

PCT Search Report and IPER issued in PCT/EP2017/055414.
Article by Popitsch et al., NGC: Lossless and lossy compression of aligned high-throughput sequencing data XP055330946, Oct. 2012.
Article by Huang et al., A privacy-preserving solution for compressed storage and selective retrieval of geomic data, XP055372050, Oct. 2016.

* cited by examiner

```
INPUT: list of position rows {P1, P2, ..., Pn}
OUTPUT: list of reads {R1, R2, ..., Rm}
read_queue = {}
for i = 1 to n do
    len <- number of base entries in Pi
    idx <- 1
    for j = 1 to len do
        if Pi[j] has a start marker then
            creat a new read R with the infomation in Pi[j]
            insert R to read_queue at position idx
            idx <- idx + 1
        elseif Pi[j] has an end marker then
            append the last base to the read read_queue[idx]
            output read_queue[idx]
            delete read_queue[idx] from the queue
        else
            append the base Pi[j] to the read read_queue[idx]
            idx <- idx + 1
        endif
    endfor
endfor
```

FIG. 7

METHODS TO COMPRESS, ENCRYPT AND RETRIEVE GENOMIC ALIGNMENT DATA

FIELD OF THE INVENTION

Methods described herein relate to genomic data processing in general, and more specifically to next generation sequencing applications.

BACKGROUND

Next-Generation Sequencing Data Processing

Next-generation sequencing (NGS) or massively parallel sequencing (MPS) technologies have significantly decreased the cost of DNA sequencing in the past decade. NGS has broad application in biology and dramatically changed the way of research or diagnosis methodologies. Advances in high-throughput sequencing technologies are spurring the production of a huge amount of genomic data. For example, the 1000 Genomes Project generated more data in its first six months than the NCBI Genbank database had accumulated in 21 years of existence. As of 2007, when the first high-throughput sequencing technology was released to the market, the growth rate of genomic data has outpaced Moore's law—more than doubling each year (http://www.genome.gov/sequencingcosts/). For example, the HiSeq X Ten System, released by Illumina in 2014, can deliver over 18,000 human genomes per year, at the price of $1000 per genome. Big data researchers estimate the current worldwide sequencing capacity to exceed 35 petabases per year. Furthermore, it is currently estimated that for every 3 billion bases of human genome sequence, 30-fold more data (about 100 gigabases) must be collected because of errors in sequencing and alignment. Even nowadays, more than 100 petabytes of storage are already used by 20 largest institutions; this corresponds to more than 1 million dollars of storage maintenance cost if we consider the Amazon cloud storage pricing (https://aws.amazon.com/s3/pricing/). This number continues to grow and 2-40 exabytes of storage capacity will be needed by 2025 for the human genomes. Hundreds of thousands of human genomes will be sequenced in the coming years, which necessitates more efficient compression approaches to genomic data storage.

Moreover, next generation sequencing data are more and more used as a tool in medical practice such as routine diagnosis, where security and privacy come as a major concern. The main threats to genomic data are (i) the disclosure of an individual's genetic characteristics due to the leakage of his/her genomic data and (ii) the identification of an individual from his/her own genome sequence. For example, as part of a clinical trial, the genetic information of a patient, once leaked, could be linked to the disease under study (or to other diseases), which can have serious consequences such as denial of access to life insurance or to employment for the individual participant. There is therefore a need for more secure genomic data management methods that address the privacy threat models that are specific to the genomic data processing systems and workflows.

Next Generation Sequencing Data Formats and Workflows

Next generation sequencers typically output a series of short reads, a few hundred nucleotides sequences with the associated quality score estimates in data files such as the FASTQ files. This raw sequencing data is further analyzed in the bioinformatics pipeline by aligning the raw short reads to a reference genome, and identifying the specific variants as the differences relative to the reference genome.

In general, geneticists prefer storing aligned, raw genomic data of the patients, in addition to their variant calls (which include each nucleotide on the DNA sequence once, hence is much more compact). Sequence alignment/map files such as the human readable SAM files and their more compact, machine-readable binary version BAM files are the de facto standards used for DNA alignment data produced by next-generation DNA sequencers (http://samtools.github.io/hts-specs/SAMv1.pdf). There are hundreds of millions of short sequencing reads (each including between 100 and 400 nucleotides) in the SAM file of a patient. Each nucleotide is present in several short reads in order to have statistically high coverage of each patient's DNA.

Genomic Data Compression

There are different approaches to dealing with the compression of genomic data. Before high-throughput technologies were introduced, there existed algorithms designed for compressing genomic sequences of relatively small size (e.g., tens of megabases), for instance BioCompress (in Grumbach, S. & Tahi, F. Compression of DNA sequences, in *Data Compression Conference*, 1993. DCC '93. 340-350), GenCompress (in Chen, X., Kwong, S. & Li, M. A Compression algorithm for DNA sequences and its applications in genome comparison. in *Proceedings of the Fourth Annual International Conference on Computational Molecular Biology* 107—ACM, 2000), and DNACompress (in Chen, X., Li, M., Ma, B. & Tromp, J. DNACompress: Fast and effective DNA sequence compression. *Bioinformatics* 18, 1696-1698-2002). These compression algorithms exploit the redundancy within DNA sequences and compress the data by identifying highly repetitive subsequences. The next generation sequencing technologies however pose new challenges for the compression of genomic data in terms of data size and structure. Due to the high similarity of DNA sequences among individuals, it is inefficient to store and transfer entirely a newly assembled genomic sequence because more than 99% of the data for two assembled human genomes are redundant. In Christley, S., Lu, Y., Li, C. & Xie, X. Human genomes as email attachments. *Bioinformatics* 25, 274-275 (2009), Christley et al proposed to store DNAzip, a reference-based compression algorithm where only differences to a reference sequence are stored. In next generation sequencing, individual sequenced data are typically organized as millions of short reads that represent short sequences, each of which comprises between 100 and 400 bases (nucleotides). Each genomic position is usually covered by multiple short reads (coverage). Li et al. (Li, H. et al. The Sequence Alignment/Map format and SAMtools. *Bioinformatics* 25, 2078-2079-2009) proposed to apply a general-purpose compression algorithm, such as BGZF (Blocked GNU Zip format—http//samtools.github.io/hts-specs/SAMv1.pdf), to these datasets as the basis for the the BAM format, the binary version of the SAM format, which is still the de facto standard of storing aligned short reads.

More recently, various advanced compression algorithms have been proposed to further improve the compression of high-throughput DNA sequence data, such as Quip (Jones, D. C., Ruzzo, W. L., Peng, X. & Katze, M. G. Compression of next-generation sequencing reads aided by highly efficient de novo assembly. *Nucl. Acids Res.* gks754-2012), Samcomp (Bonfield, J. K. & Mahoney, M. V. Compression of FASTQ and SAM Format Sequencing Data. *PLoS ONE* 8, e59190-2013), HUGO (Li, P. et al. HUGO: Hierarchical Multi-reference Genome Compression for aligned reads. *Journal of the American Medical Informatics Association* 21, 363-373-2014), and CRAM, a reference-based compression algorithm for aligned data (Fritz, M. H.-Y., Leinonen, R., Cochrane, G. & Birney, E. Efficient storage of high throughput DNA sequencing data using reference-based compression. *Genome Res.* 21, 734-740-2011). CRAM is used for instance by the 1000 genomes project (http://www.1000genomes.org/). Most of these algorithms use conventional entropy coding techniques, such as Huffman variable-length encoding, Golomb, or arithmetic coding, to compress the metadata text strings (e.g., read name, position, mapping quality, etc.). Recently, Massie et al. (Massie, M. et al. Adam: Genomics formats and processing patterns for cloud scale computing. *EECS Department, University of California, Berkeley, Tech. Rep. UCB/EECS*-2013-207-2013) proposed ADAM, a cloud-computing framework for genomic data compression, which combines various data compression engineering techniques such as dictionary coding and gzip compression in combination with distributed processing to reduce 25% of the storage costs compared to the BAM de facto standard. The ADAM scheme also achieves significant (2-10×) speedup in decompression performance for genomics data access patterns.

Genomic Data Security

Some genomic data encryption solutions have been proposed on top of some compression algorithms, such as for instance the encryption option in cramtools for the CRAM genomic data compression format (http://www.ebi.ac.uk/ena/software/cram-toolkit), but they remain straightforward applications of encryption standards and do not take into consideration the specific genomic data storage and genomic data processing threat models even if the solution uses highly secure encryption primitives (e.g., the AES encryption method). In particular, the data retrieval process may cause incidental leakage of sensitive genomic information. Once leaked, genomic information could be abused in various ways, such as for denial of employment and health insurance, blackmail or even genetic discrimination. Establishing a secure and privacy-preserving solution for genomic data storage is therefore needed in order to facilitate the trusted usage, storage and transmission of genomic data.

Recent research works have thus highlighted a number of specific threats to be addressed by genomic data security and privacy-preserving technologies. For instance, public aggregated statistics in genome-wide association studies (GWAS) may lead to a potential privacy breach for participants of the study, because attackers can determine, through powerful statistical tests, whether a participant is in a case group (Homer, N. et al. Resolving Individuals Contributing Trace Amounts of DNA to Highly Complex Mixtures Using High-Density SNP Genotyping Microarrays. *PLoS Genet* 4, e1000167-2008). Data de-identification (removal of the personal identifiers) has also been proven insufficient for protecting genetic privacy (Erlich, Y. & Narayanan, A. Routes for breaching and protecting genetic privacy. *Nat Rev Genet* 15, 409-421-2014). Coarse-grained encryption and access control to genomic data may also lead to incidental genomic findings that doctors would prefer to avoid (Ayday, E., Raisaro, J. L., Hengartner, U., Molyneaux, A. & Hubaux, J.-P. Privacy-Preserving Processing of Raw Genomic Data. in *Data Privacy Management and Autonomous Spontaneous Security*, 133-147-Springer Berlin Heidelberg, 2014).

Storing sequenced data on a cloud seems to be an attractive option, considering the size and the required availability of the data, so that it can be more easily shared by different parties. Accessing the remote data stored with standard compression schemes require to decrypt it first so the data owner has to trust insiders on the cloud (e.g., the cloud administrator, or high-privileged system software) to access the genomic information in the clear and multi-party key management systems have to be carefully designed accordingly. Ayday et al. (Ayday, E., Raisaro, J. L., Hengartner, U., Molyneaux, A. & Hubaux, J.-P. Privacy-Preserving Processing of Raw Genomic Data. in *Data Privacy Management and Autonomous Spontaneous Security*, 133-147—Springer Berlin Heidelberg, 2014 and WO2014/202615) proposed the use of order-preserving encryption to enable genetic data retrieval without requiring full decryption of the genomic data. While it addresses the security issues associated with genomic information privacy threats, the latter scheme requires further data overhead, which induces extra storage and processing costs requirements and make it impractical for certain clinical genomic applications.

Therefore, it will be of great benefit to the future development of sequenced data analysis if a compression solution can also integrate encryption methods that are secure and suitable for preserving the privacy of genomic information in the decompression and decryption process.

Genomic Data Access

For clinical or research purpose, the most valuable information from human genomic data is the set of genetic variants that are identified among the three billion genome positions. However, current state-of-the-art sequencers produce millions of short reads, scattered over the whole genome and covering each position multiple times. Typically, sequenced data are taken as input for a pipeline and retrieved for downstream analyses, e.g., variant calling. Taking this usage scenario into account, it is also crucial to have a storage format that is efficient for downstream analyses. For example, it is a common practice to aggregate information on a position from all short reads that cover the position (pileup), hence it is desirable that the storage format organizes information in this manner.

An increasing number of medical units (pharmaceutical companies or physicians) are willing to outsource the storage of genomes generated in clinical trials. As the medical unit would not own the genome, this is a good argument to convince clinical-trial participants to be sequenced and use their genomes to stratify clinical trials. Acting as a third party, a biobank storage unit could store patients' genomic data that would be used by the medical units for clinical trials. In the meantime, the patient can also benefit from the stored genomic information by interrogating his own genomic data, together with his family doctor, for specific genetic predispositions, susceptibilities and metabolical capacities. The major challenge here is to manage the data access rights to preserve the privacy of patients' genomic data while allowing the medical units to operate on specific parts of the genome (for which they are authorized). In WO2014/202615, Ayday et al. proposed a privacy-preserving genomic data processing system based on order-preserving encryption that is suitable to encrypt, store and facilitate the private partial retrieval of aligned genomic data files such as SAM files in a biobank. However this system does not address the storage compression efficiency and there is therefore a need to further improve it.

In addition to combining the compression and encryption of next-generation-sequencing (NGS) data for efficient and privacy-preserving storage, this would also require us to consider who can access the data, which part they can access and how the data can be partially retrieved. Without these precautions, there could be incidental leakage during data retrieval, even if it is stored in an encrypted form. Furthermore, the storage and access efficiency of sequenced data needs to be further optimized without compromising the security requirements. Better methods and systems to process genomic data information are needed that consistently address all these problems (security and privacy, storage, partial retrieval) to minimize the storage cost without compromising the privacy of genomic data information while optimizing the performance of downstream analysis (e.g., variant calling).

BRIEF SUMMARY

Some embodiments of the present disclosure are directed to methods to encode genomic data alignment information organized as a read-based alignment information data stream, comprising the steps of: transposing, with a processor, the read-based alignment information data stream into a position-based alignment information data stream; encoding, with a processor, the position-based alignment information data stream into a reference-based compressed position data stream; and encrypting, with a processor, the reference-based compressed position data stream into a compressed encrypted alignment data stream.

In some embodiments, encoding the position-based alignment information data stream into a reference-based compressed position data stream may comprise a step of differential encoding. In a possible embodiment, differential encoding may comprise recording, for each position in the reference-based compressed position data stream, the alignment differences relative to the alignment reference sequence. In a possible embodiment, encoding the position-based alignment information data stream into a reference-based compressed position data file may comprise a step of entropy coding.

In some embodiments, encrypting the reference-based compression position data stream into a compressed encrypted alignment data stream may comprise a step of encrypting the position information with an order-preserving encryption scheme. In a possible embodiment, encrypting the reference-based compression position data stream into a compressed encrypted alignment data stream may comprise a step of encrypting the position-based alignment information with a symmetric encryption scheme. The symmetric encryption scheme may be a stream cipher, such as the AES scheme in CTR mode.

Some embodiments of the present disclosure are directed to methods to retrieve genomic data alignment information from a compressed encrypted alignment data stream, recorded on a storage unit, comprising the steps of: receiving a genomic alignment range query [Pos1, Pos2] from a genomic data analysis system; retrieving from the storage unit, with a processor, the subset of the compressed encrypted alignment data stream corresponding to the genomic alignment range [Pos1, Pos2] in the compressed encrypted alignment data stream; decrypting, with a processor, the compressed encrypted alignment data stream into a reference-based compressed position data stream corresponding to the genomic alignment range [Pos1, Pos2]; and decoding, with a processor, the reference-based compressed position data stream into a position-based alignment information data stream corresponding to the genomic alignment range [Pos1, Pos2].

In a possible embodiment, retrieving genomic data alignment information from a compressed encrypted alignment data stream, recorded on a storage unit, may further comprise a step of reverse transposing, with a processor, the position-based alignment information data stream into a read-based alignment information data.

In a possible embodiment, retrieving the subset of the compressed encrypted alignment data stream for the genomic alignment range [Pos1, Pos2] comprises retrieving the symmetric encrypted data and the metadata stored in data blocks between the order-preserving encrypted position associated with Pos1 and the order-preserving encrypted position associated with Pos2.

In a possible embodiment, decrypting the compressed encrypted alignment data stream into a reference-based compressed position data stream corresponding to the genomic alignment range [Pos1, Pos2] comprises symmetric decryption of the symmetric encrypted data between the order-preserving encrypted position associated with Pos1 and the order-preserving encrypted position associated with Pos2. In a possible embodiment, the symmetric decryption scheme may be a stream decipher, such as the AES scheme in CTR mode.

In a possible embodiment, decoding the position-based alignment information data stream into reference-based compressed position data stream may comprise a step of entropy decoding. In a possible embodiment, decoding the position-based alignment information data stream into reference-based compressed position data stream may comprise a step of differential decoding.

BRIEF DESCRIPTION OF THE DRAWINGS

FIG. 7 shows a pseudo-code algorithm that may be used to integrally reconstruct a read-based data structure from the proposed position-based data structure.

DETAILED DESCRIPTION

Genomic Data Encoder

Figure 1:
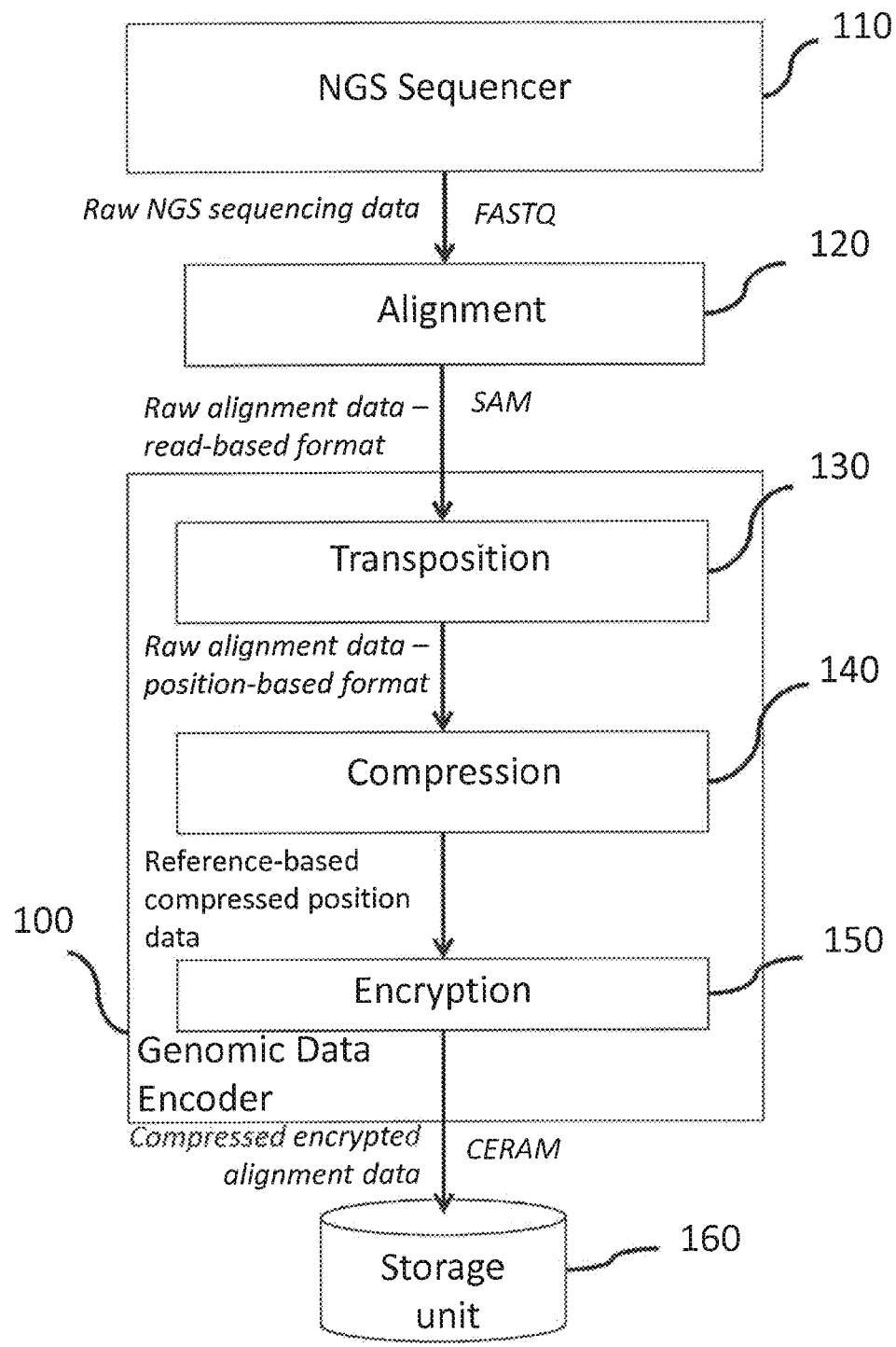
FIG. 1 shows a genomic data encoding system in accordance with certain aspects of the present disclosure.

FIG. 1 shows a genomic data processing system comprising a genomic data encoder 100, a next generation (NGS) sequencer 110 and a biobank storage unit 160. The next generation sequencer 110 may generate, with a processor, raw NGS sequencing data in one or more data files. In a possible embodiment the raw sequencing data file may be in the FASTQ format as known to those skilled in the art of bioinformatics for next generation sequencing technologies. Depending on the NGS technology, one or more files may be output by the NGS sequencer 110. In some embodiments, the FASTQ file format may be used with two different files for forward and reverse reads or as a single joined file. Other embodiments are also possible.

With a processor, an alignment module 120 may take as input the raw NGS sequencing data, align the short reads to a reference genome, and generate a raw alignment data file. In a possible embodiment the raw alignment data file may be in the SAM format, a read-based format, as known to those skilled in the art of bioinformatics. In another possible embodiment (not illustrated), the raw alignment data file may be in the BAM format, the binary equivalent of the SAM format.

The alignment module 120 may be programmed or otherwise configured to implement different genomic data alignment methods, as known to those skilled in the art of bioinformatics. The alignment module 120 may be a computer system or part of a computer system including a central processing unit (CPU, "processor" or "computer processor" herein), memory such as RAM and storage units such as a hard disk, and communication interfaces to communicate with other computer systems through a communication network, for instance the internet or a local network. In some embodiments, the computer system may comprise one or more computer servers, which may enable distributed computing, such as cloud computing, for instance in a genomic data farm. In some embodiments, the alignment module 120 may be integrated into a massively parallel system. In some embodiments, the alignment module 120 may be directly integrated into a next generation sequencing system.

A genomic data encoder 100 may take as input the raw alignment data out of the alignment module 120; transpose it, with a transposition module 130, into a position-based raw alignment data file; compress, with a compression module 140, the position-based raw alignment data file into a reference-based compressed position data file; and encrypt, with an encryption module 150, the reference-based compressed position into a data file enabling *Selective retrieval on Encrypted and Compressed Reference-oriented Alignment Map* («SECRAM» file format). In a possible embodiment, the genomic data encoder 100 may record the resulting encrypted compressed alignment SECRAM data file into a biobank storage unit 160. In other possible embodiments (not illustrated), the genomic data encoder 100 may directly transmit the encrypted compressed alignment SECRAM data file to a bioinformatics analysis pipeline.

The genomic data encoder 100 computer system (also "system" herein) may be programmed or otherwise configured to implement different genomic data processing methods, such as transposing and/or converting and/or compressing and/or encrypting alignment data.

The genomic data encoder 100 may be a computer system or part of a computer system including a central processing unit (CPU, "processor" or "computer processor" herein), memory such as RAM and storage units such as a hard disk, and communication interfaces to communicate with other computer systems through a communication network, for instance the internet or a local network. In some embodiments, the computer system may comprise one or more computer servers, which may enable distributed computing, such as cloud computing, for instance in a genomic data farm. In some embodiments, the genomic data encoder 100 may be integrated into a massively parallel system. In some embodiments, the genomic data encoder 100 may be directly integrated into a next generation sequencing system.

Other embodiments are also possible. For instance, while most genomic data compression algorithms have been conceived as lossless to preserve the original data content, Yu et al. (Yu, Y. W., Yorukoglu, D., Peng, J. & Berger, B. Quality score compression improves genotyping accuracy. *Nat Biotech* 33, 240-243-2015) recently proposed QUARTZ, a lossy-compression algorithm, which can be used to discard 95% of quality scores out of the FASTQ raw sequencing data files, that is prior to alignment, without losing accuracy of downstream analysis. Their method works on the FASTQ file stage and may be implemented by a pre-processing module (not illustrated) operating between the NGS sequencer 110 and the alignment module 120 in order for the end-to-end system to achieve a higher overall compression ratio.

Transposition

Figure 2A:
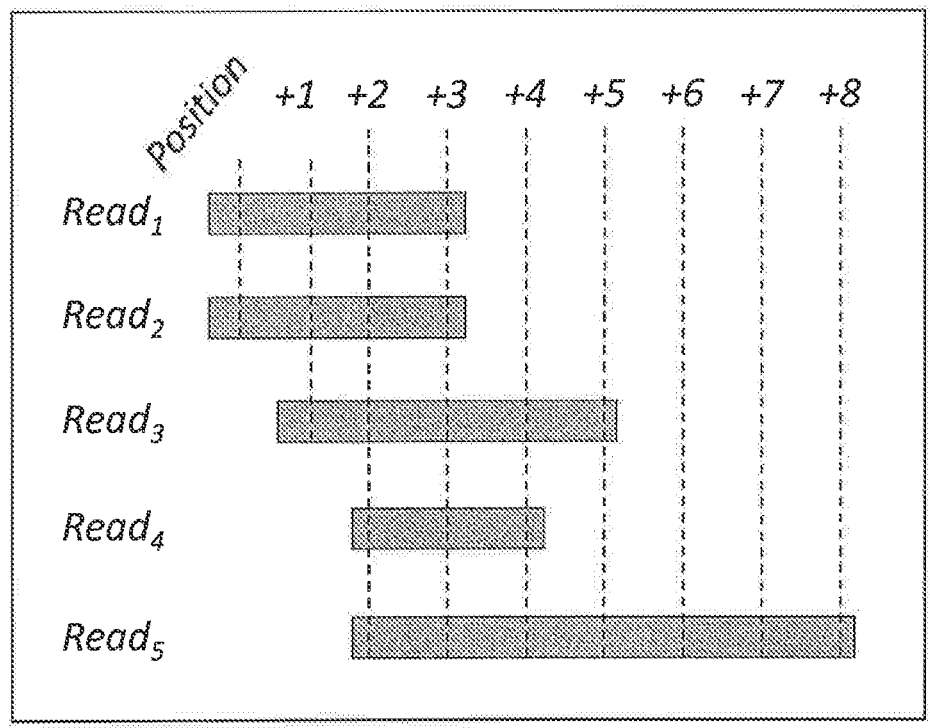
FIG. 2A shows an abstract representation of a read-based storage format and FIG. 2B shows an abstract representation of its transposition as a position-based storage format.
Figure 2B:
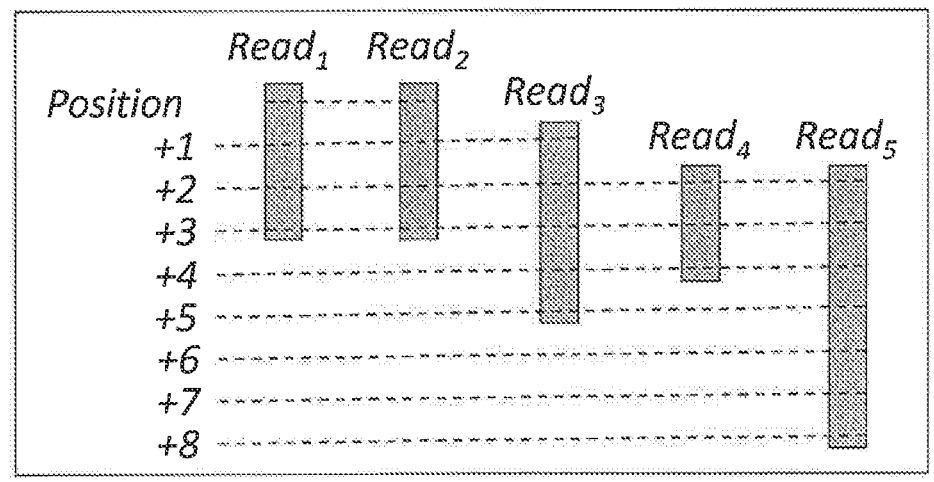

In a preferred embodiment, the transposition module 130 converts the genomic alignment information from a read-based data structure, as illustrated in FIG. 2a, into a position-based data structure, as illustrated in FIG. 2b. In a read-based format (FIG. 2a) the aligned data, represented by short reads, are sequentially stored as generated by the sequencer 110, read-by-read, in a raw alignment data file.

Examples of commonly used read-based formats include the SAM format, the BAM format and the CRAM format. In a position-based format (FIG. 2b), information about one position is clustered together into a continuous storage, hence the aligned data are stored position-by-position in a file. An example of a position-based format is the ADAM format as proposed by Massie in 2013 to achieve more efficient compression, both in terms of alignment data storage efficiency and alignment data retrieval computational efficiency (Massie, M. et al. Adam: Genomics formats and processing patterns for cloud scale computing. *EECS Department, University of California, Berkeley, Tech. Rep. UCB/EECS*-2013-207-2013).

Figure 3:
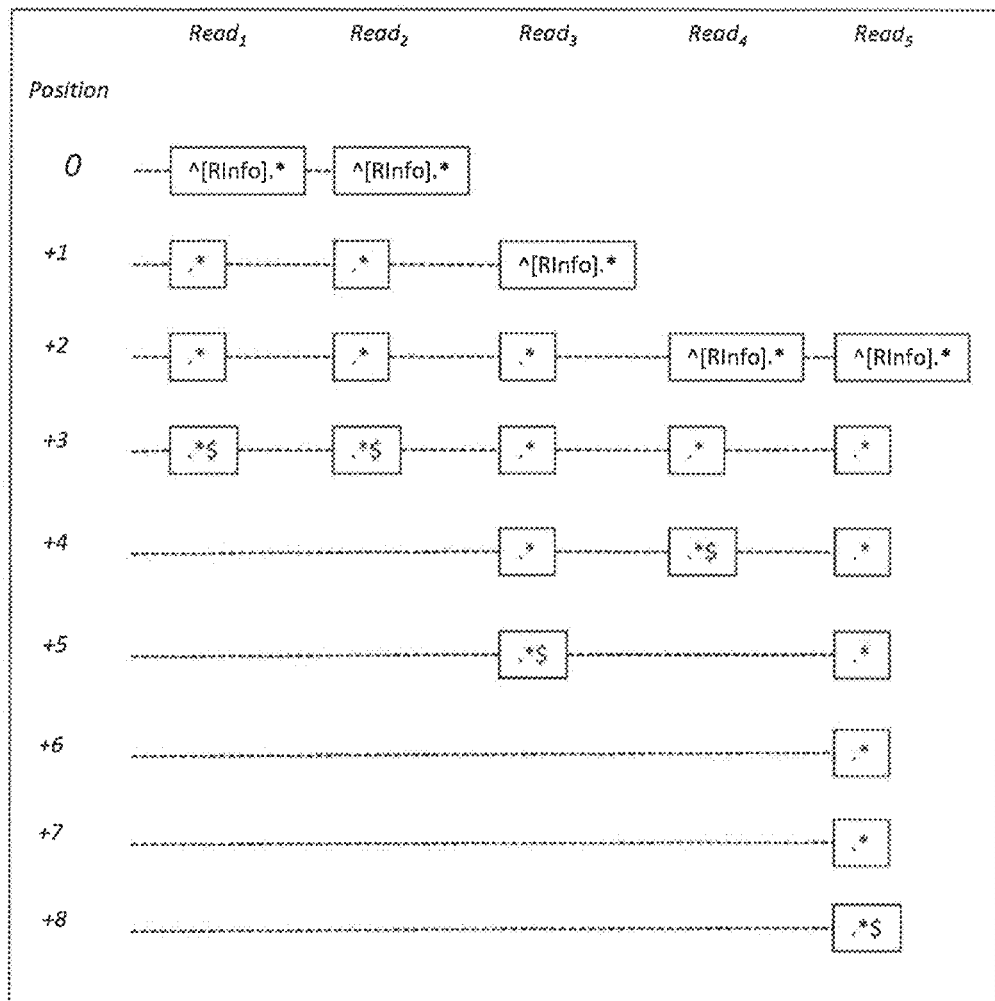
FIG. 3 shows an example of a position-based data file structure.

FIG. 3 shows an example of a position-based data file structure for 5 reads (Read1, Read2, Read3, Read4, Read5) overlapping 9 positions indexed from 0 to 8. At position 0 the start marker of Read1 and Read2 is recorded. In a possible embodiment, as illustrated in FIG. 3, the '^' character may be used as the start marker for each short read start in the data text file, followed by metadata information regarding the short read such as its name or id, strand, and/or mapping quality, and the nucleotide base identified at this position (A, T, C or G, denoted '.*' in FIG. 3) with the associated quality score, but other embodiments are also possible. At position +1 the continuation of Read 1 and Read2, that is the next nucleotide base identified at this position (A, T, C or G, denoted '.*' in FIG. 3), as well as the start of Read 3, are recorded. At position +3, the last base of Read1 and Read2, followed by the end marker of Read 1 and Read2, as well as the continuation of Read3, Read4 and Read5 respectively, that is the next nucleotide base identified at this position (A, T, C or G, denoted '.*' in FIG. 3) for Read3, Read4 and Read5 respectively, are recorded. In a possible embodiment, as illustrated in FIG. 3, the '.*$' character may be used as the end marker for each short read end in the data text file, but other embodiments are also possible. For the sake of illustration, only ultra short reads overlapping 3 (read4) to 7 (read5) positions have been illustrated in FIG. 3, but the proposed data structure is of course applicable to short reads of 100 bp and beyond, as commonly output by NGS sequencers. Also one skilled in the art of data compression will also note that the longer the read, the shorter the RInfo metadata overhead in the resulting position-based data file structure. In a possible embodiment (not illustrated), the read information Rinfo may also include the read length so that the end marker does not need to be recorded.

Compression

In a preferred embodiment, the compression module 140 may compress the position-based raw alignment data file into a reference-based compressed position data file. In a possible embodiment, the compression may comprise a first step of reference-based compression, where the position information is compared to the reference sequence (as used in the alignment step) and only the differences of a position with respect to that of the reference are recorded.

Properly aligned short reads shall share significant redundancy, as a large portion of most reads are likely to match the reference. For instance, in FIG. 2, Read1 and Read2 data shall be very similar. In a possible embodiment of reference-based compression, a position cigar string (PosCigar) may be extracted from the position-based raw alignment data. For a given position, all reads that cover the position may be ordered by their starting positions, then each read is attached with a unique order. Other embodiments are also possible, for instance a reverse order may be used, or a specific bundling of pair-ended reads may be used when the sequencer outputs pair-ended reads (e.g. Illumina sequencer). Note that one read may be assigned a different order for different positions because the corresponding lists of covered reads in those positions vary. At any single position, the PosCigar string may capture one or more of three different primitive alignment difference operators, such as:
1. SUBSTITUTION—Order ||'S'||[A|T|C|G]: the read (specified by Order) has a substitution with the specified letter compared to the reference.
2. INSERTION—Order ||'I'||i||{A,T,C,G}$^i$: the read has an insertion of i letters that are listed.
3. DELETION—Order||'D': the read has a deletion.

Figure 4:
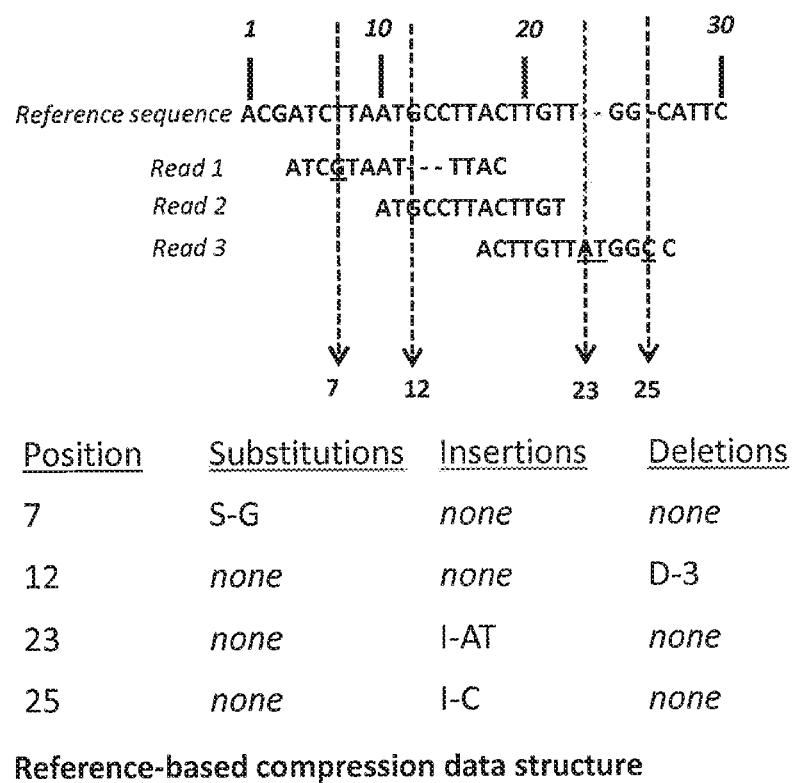
FIG. 4 shows an example of a reference-based compression data structure.

For example, a PosCigar that looks like "9I4ATIG . . . 23SA . . . 57D", means:
9I4ATG: an insertion of 4 letters "ATTG" in the 9 read
23SA: a substitution with letter 'A' in the 23$^{th}$ read
57D: a deletion in the 57$^{th}$ read A simple example of the proposed reference-based compression data structure is illustrated in FIG. 4 where:
the PosCigar at position 7 refers to 1SG (substitution with base 'G' in Read1 ordered as read #1 at that position)
the PosCigar at position 12 refers to 1D3 (deletion of 3 bases in Read1 ordered as read #1 at that position)
the PosCigar at position 23 refers to 1IAT (insertion of 2 bases 'A','T' in Read3 ordered as read #1 at that position)
the PosCigar at position 25 refers to 1IC (insertion of base 'C' in Read3 ordered as read #1 at that position)

More complex alignment difference operators (e.g., soft clipping, hard clipping, skipping region . . . ) may also be encoded by the aforementioned primitives operators, or a combination thereof as will be apparent to those skilled in the art.

In a possible embodiment, each position row may then be encoded as:
Row size||Position||List of read headers||Quality scores-||PosCigar
Where:
Row size is the length (measured by bytes) of a position row;
List of read headers lists the reads that start at this position. It is decomposed as (Order||RInfo)*, with "*" meaning an arbitrary number of such headers. In a possible embodiment, the read information RInfo may also include the read length so that we do not have to store the end marker.
Quality scores records the quality scores for the bases of this position.
PosCigar records the variants information relative to the reference sequence.

Once the position-based raw alignment data has been transformed into a reference-based compressed position data structure, one skilled in the art of data encoding may apply additional data encoding techniques such as entropy coding and/or text coding algorithms to further compress the data into a compact, binary reference-based compressed position data file. In a possible embodiment, variable length coding may be used to further compress the differences found in reference-based compression, and also the metadata of a read, such as the mapping quality scores.

Depending on the content of the information, for instance on the metadata of a read, such as the string of mapping quality scores, the most efficient encoding technique may be selected, such as Huffman, Golomb and Beta encodings. In a possible embodiment, encoding methods similar to the CRAM compression techniques may be used, as known to those skilled in the art (https://www.ebi.ac.uk/ena/software/cram-toolkit). In an alternative embodiment, arithmetic coding may be used, similar to the QUIP compression techniques as known to those skilled in the art (https://github.com/dcjones/quip). In a possible further embodiment, multiple position rows may be grouped into a data block and further block compression such as the gzip algorithm may be used after the entropy coding stage to improve the compression of text information such as read name, quality scores and other auxiliary text information. In a possible embodiment, multiple position rows, for instance 50000 rows, may be grouped in a single block, and multiple blocks may be processed in parallel, but other embodiments are also possible. Various combinations of the aforementioned entropy coding and/or text encoding methods and/or block coding methods may also be used, as will be apparent to those skilled in the art of data compression. In a possible embodiment, different fields corresponding different data structures in the metadata may be compressed with a different technique, so as to fine-tune the final compression in accordance with the statistical distribution specifics of each data structure.

Encryption

In a possible embodiment, the encryption module 150 may assign a master key $K_m$ to each patient, that may be used to derive various encryption keys for different encryption steps. The encryption module 150 independently encrypts the variant information for each position, that is each row in the data structure of FIG. 3, so as to provide fine-grained privacy control by enabling partial genomic alignment data retrieval while addressing the overall genomic alignment information leakage threats. Thus, as will be apparent to one skilled in the art of bioinformatics for next generation sequencing technologies, it is possible to restrict data retrieval to only the positions of interest from the resulting data file (for instance in the a «SECRAM» file format) without leaking any information from positions out of the region of interest, even if the original read alignment data (for instance in the SAM/BAM file format) covers both relevant and irrelevant positions.

Figure 5A:
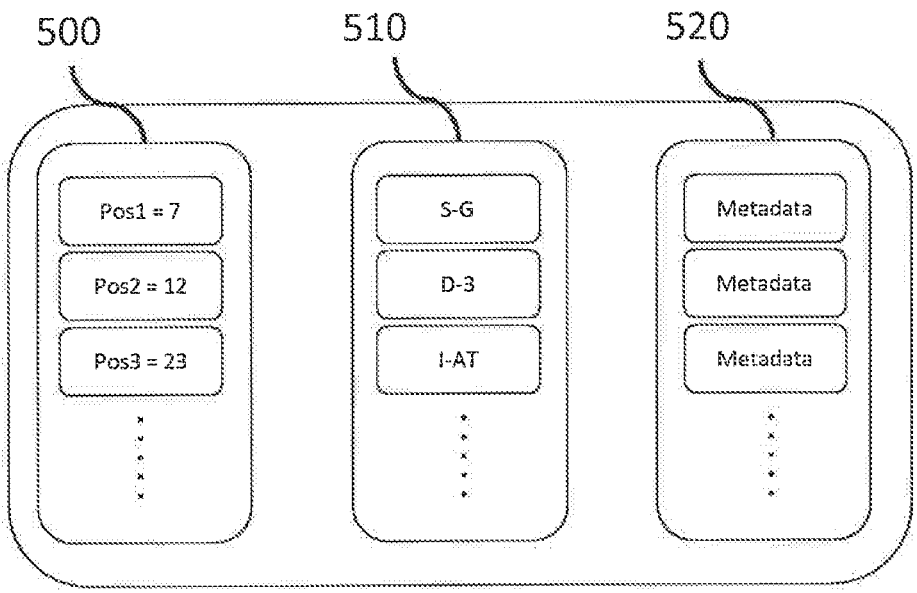
FIGS. 5A and 5B illustrate a possible encryption format in accordance with one aspect of the present disclosure.
Figure 5B:
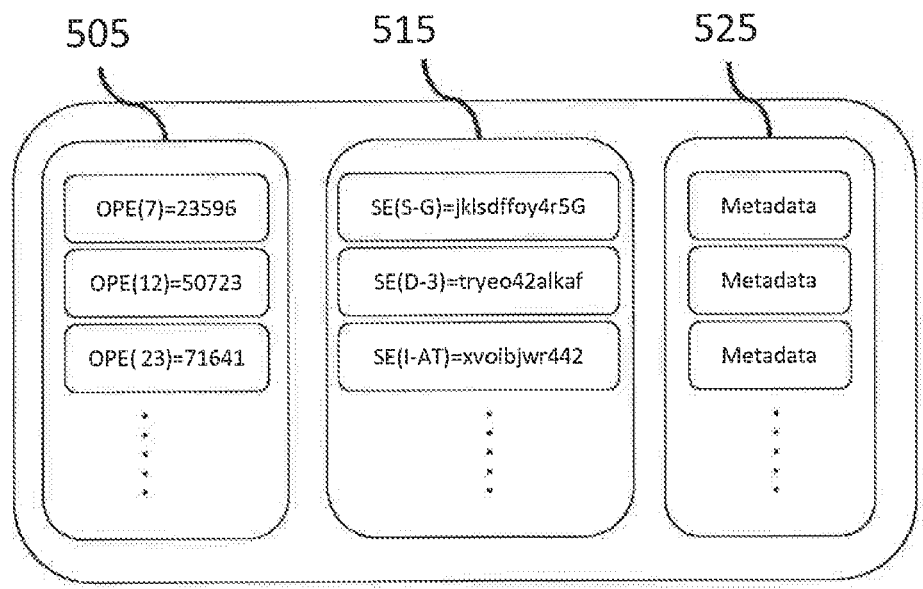

In a preferred embodiment, the encryption module 150 encrypts the compressed genomic data file format of FIG. 5a) into an encrypted compressed SECRAM file format as illustrated on FIG. 5b) in two steps. In a first step the encryption module 150 derives an order-preserving encryption key $K_{ope}$ from the patient master key $K_m$ and encrypts the position fields Pos1, Pos2, Pos3 . . . into an order-preserving encrypted block of positions 505 from the compressed genomic data file block 500 by using an order-preserving encryption (OPE) scheme with the order-preserving encryption key $K_{ope}$, such as the one described by Boldyreva et al (Boldyreva, A., Chenette, N. & O'Neill, A. in Order-Preserving Encryption Revisited: Improved Security Analysis and Alternative Solutions. in *Advances in*

Cryptology—CRYPTO 2011, 578-595—Springer Berlin Heidelberg, 2011). This order-preserving encryption scheme enables the retrieval of the resulting encrypted data 505 at a given row corresponding to a specific position (OPE(Pos1), OPE(Pos2), or OPE(Pos3) . . . in FIG. 5) without requiring the decryption of the whole block of data 505 (for instance, a block of 50000 data rows) at decoding stage.

In a second step, with reference to the format of FIG. 5, the encryption module 150 encrypts the sensitive information at each position, such as the block 510 of PosCigar data S-G, D-3 I-AT . . . of encoded short read differences relative to the reference sequence, into an encrypted block 515 of PosCigar data with a state of the art security encryption method SE. A possible embodiment of the second encryption step may be detailed as follows. The encryption module 150 derives a key $K_{sc}$ from the patient master key $K_m$. For the $i^{th}$ block 510 covering several position rows in its input reference-based compressed position data file associated with patient m, the encryption module 150 generates a random salt $R_i$. For each position row in compressed block i, the encryption module 150 encrypts the concatenated PosCigar data 510 with a stream cipher using the symmetric cipher key $K_{sc}$ and the random salt $R_i$ to generate the symmetrically encrypted PosCigar data 515. In a possible embodiment an XOR stream cipher mode is used for encryption. In a possible embodiment AES in the CTR stream cipher mode is used. In a possible embodiment the encryption module 150 stores the random salt $R_i$ in an index file (not illustrated). In another possible embodiment (not illustrated) the encryption module 150 stores the random salt $R_i$ in the header of the encrypted data block 515.

In a possible embodiment, with reference to the FIG. 5 format, the other data fields 520, such as the block size, the list of read headers and/or the quality scores metadata 520 may be left in clear format 525, because they do not contain any highly sensitive information. Other embodiments are also possible.

As will be apparent to those skilled in the art of cryptography, other embodiments of the first and second encryption steps are also possible. For instance in a possible different embodiment, the first and second encryption steps may be applied in the reverse order. They may be conducted in parallel by different processors in the encryption module 150, as they are independent. Various order-preserving encryption schemes may be used to encrypt the position information 500 as the cryptanalysis progresses in this relatively recent field of cryptography research—for instance, enhancements to the Boldyreva scheme recently proposed respectively by Chenette et al. (Chenette, N., Lewi, K., Weis, S. A. & Wu, D. J. Practical Order-Revealing Encryption with Limited Leakage. *Cryptology ePrint Archive*—2015), by Kerschbaum (Kerschbaum, F. Frequency-Hiding Order-Preserving Encryption. in *Proceedings of the 22Nd ACM SIGSAC Conference on Computer and Communications Security* 656-667—ACM—2015), or by Roche et al. Roche, D., Apon, D., Choi, S. G. & Yerukhimovich, A. POPE: Partial Order-Preserving Encoding. *Cryptology ePrint Archive*—2015) may be used in alternate embodiments of the proposed methods and systems. Various standard symmetric encryption schemes may also be used to encrypt the PosCigar information 510.

As will be understood by those skilled in the art of communications security, the overall scheme security and privacy enforcement is strongly dependent on the underlying key management system. The encryption may for instance be done according to the method and system described in the PCT Patent Publication WO2014/202615 entitled "Method to manage raw genomic data in a privacy preserving manner in a biobank", the entirety of which is incorporated by reference herein, but the encryption scheme is not limited to this approach.

Indexing

In order to facilitate random access to the compressed encrypted data file, an index of aligned genomic data may be built by the genomic data encoder 100 in a post-processing stage (not illustrated) by mapping from positions to file offsets such that, given queried positions, a data reader can directly access the relevant part in the file and recording them into a companion index file. As will be apparent to those skilled in the art of data management, indexing is easier in the proposed compressed encrypted scheme (e.g. SECRAM file format) than in the prior art BAM scheme because it does not require the complicated binning scheme used in a BAM index file. In a possible embodiment, the index file contains a list of tuples (position; file offset) wherein "position" is the genomic position in the reference sequence of the first position row in a data block, and "file offset" is the byte offset into the compressed file to the beginning of said data block. The index file may also store the side encryption information, such as the random salt $R_i$ associated with the $i^{th}$ encrypted data block 515, but other embodiments are also possible. The index file may then be referred to by the genomic data decoder querying a partial genomic alignment data retrieval to facilitate a more efficient data access in the compressed encrypted file.

Genomic Data Decoder

Figure 6:
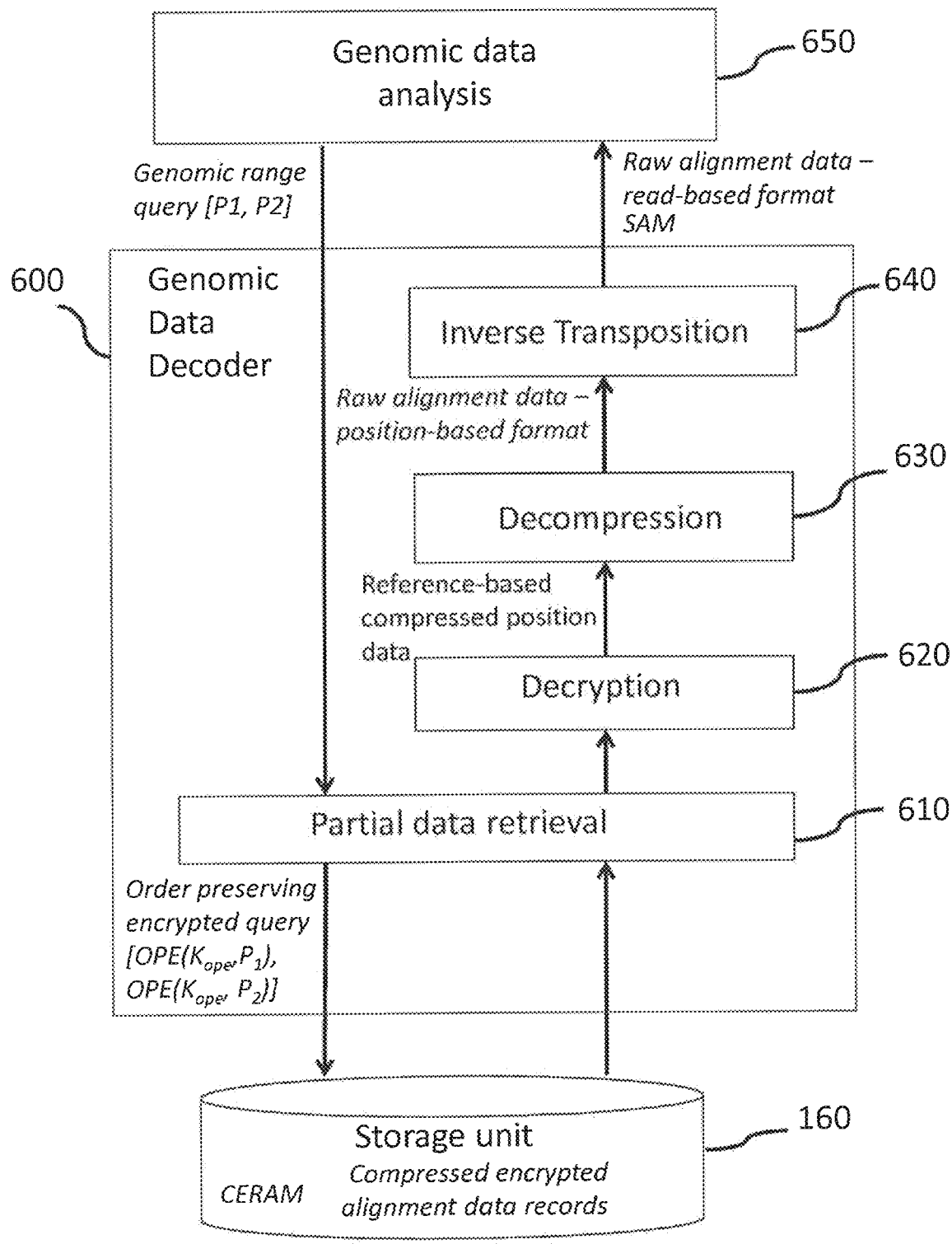
FIG. 6 shows a genomic data decoding system in accordance with certain aspects of the present disclosure.

FIG. 6 shows a genomic data processing system comprising a biobank storage unit 160, a genomic data decoder 600, and a genomic data analysis system 650. The biobank storage unit 160 may store, in its memory, the genomic alignment data information for a given patient as a data file, for instance in the SECRAM file format, according to the aforementioned genomic data encoding methods and systems. A genomic data analysis system 650 may query the genomic alignment data of a given patient for a specific position range $[P_1,P_2]$ in the alignment reference sequence, such as for instance the position range corresponding to a coding exon region out from a specific gene for which variants have to be analyzed (e.g. variant calling) by the genomic data analysis system 650.

In a possible embodiment (not illustrated), for instance in accordance with to the method and system architecture described in the PCT Patent Publication WO2014/202615 entitled "Method to manage raw genomic data in a privacy preserving manner in a biobank", the entirety of which is incorporated by reference herein, the genomic data analysis system 650 may be operated by a medical unit (MU) specializing in the diagnostic and treatment of a disease corresponding to a specific genomic region, such as exons associated with the BRCA1 and BRCA2 genes in female breast and ovarian cancers. The genomic data decoder 600 may comprise a masking and key manager (MK) unit in charge with handling the master key $K_m$ for each patient, and the communications between the medical unit MU and the masking and key manager (MK), in particular the genomic range query $[P_1,P_2]$, may be encrypted with a one-time symmetric session key $K_{ss}$. Other embodiments are also possible.

The genomic data decoder 600 may comprise a partial data retrieval module 610 to retrieve, with a processor, only the compressed encrypted alignment data corresponding to the specific position range $[P_1, P_2]$ from the biobank storage unit 160 without needing to retrieve the whole patient alignment data. The genomic data decoder 600 may further comprise a decryption module 620, a decompression module 630 and an inverse transposition module 640 to decrypt, decode and reconstruct with a processor, the read-based alignment data corresponding to the queried range [$P_1$, $P_2$], for the genomic data analysis system 650. In a possible embodiment the genomic data decoder 600 may reconstruct the read-based alignment data file in the SAM file format, but other embodiments are also possible. In another possible embodiment (not illustrated), the genomic data analysis system 650 may directly process the raw position-based alignment data format out of the decompression module 630, so that the inverse transposition is not needed, thus resulting in a more computationally efficient overall workflow.

The genomic data decoder 600 computer system (also "system" herein) may be programmed or otherwise configured to implement different genomic data processing methods, such as searching and/or querying and/or decrypting and/or decoding and/or transposing genomic information data.

The genomic data decoder 600 may be a computer system or part of a computer system including a central processing unit (CPU, "processor" or "computer processor" herein), memory such as RAM and storage units such as a hard disk, and communication interfaces to communicate with other computer systems through a communication network, for instance the internet or a local network. In some embodiments, the computer system may comprise one or more computer servers, which may enable distributed computing, such as cloud computing, for instance in a genomic data farm. In some embodiments, the genomic data decoder 600 may be integrated into a massively parallel system. In some embodiments, the genomic data decoder 600 may be directly integrated into a biobank system comprising a biobank storage unit 160.

Partial Data Retrieval with Order-Preserving Decryption

In a possible embodiment, the partial data retrieval module 610 only needs to retrieve the genomic alignment data within the queried range of positions [$P_1$, $P P_2$] in the compressed encrypted file stored on the storage unit 160. As the position information has been encrypted with an order-preserving encryption scheme, the partial data retrieval module 610 does not need to decrypt the position data to retrieve the associated content; it may simply retrieve the symmetric encrypted data 515 and the metadata 525 stored in data blocks between the order-preserving encrypted positions 505 [OPE($K_{ope}$, $P_1$), OPE($K_{ope}$, $P_2$)]. Using the index file, for each block $B_i$, the data retrieval module 610 first locates the compressed encrypted data block $B_i$ containing the order-preserving encrypted position and extracts the offsets of the k data blocks ($B_i$, $B_{i+1}$, ..., $B_{i+k-1}$) that overlap with the range [OPE($K_{ope}$,$P_1$), OPE($K_{ope}$,$P_2$)], then a linear search locates each order-preserving encrypted position in the data block. For each block $B_i$, the data retrieval module 610 then determines the position offset of the encrypted PosCigar string information 515 in the data block $B_i$ as an offset from the matching order-preserving encrypted position in the data block. The data retrieval module 610 also extracts the random salt $R_i$ associated with the $i^{th}$ encrypted data block 515 from the index file or the header of the $i^{th}$ encrypted data block 515, depending on the actual encoding embodiment.

In most cases, the queried range of positions [$P_1$,$P_2$] may only be partially overlapped with some of the reads, e.g., the starting position of a read may be before the $P_1$ position. In the aforementioned possible embodiment of the SECRAM file format encoding where the metadata information block 525 (read name, strand, mapping quality, read flags, etc.) is recorded only at the starting position of a read, the partial retrieval module 610 may retrieve said metadata information by searching back to that position in the SECRAM file, after locating the starting position of the query from the index file. If the position row $P_1$ contains any read that is not complete in block $B_i$ (specifically, it does not start at this block), the partial retrieval module 610 may trace it back to the previous block(s) $B_{i-1}$ ($B_{i-2}$), extract and crop the corresponding metadata fields for the incomplete reads recorded at the position $P_1$ row in the data block $B_i$. Note that for a block encoding size significantly over the average read size, for example a block size of several thousands of positions while the average read size is of 100 bp order of magnitude, the partial data retrieval module 610 typically needs to look back to at most one previous block $B_{i-1}$. The partial data retrieval module then retrieves these metadata fields along with the complete data in the query range [$P_1$,$P_2$].

For queries related to a complete read recorded between start position $P_1$ and end position $P_2$, the partial data retrieval module 610 may also first extract the associated metadata field 525 for a first read at a given position and cache said metadata field at said position to enable faster retrieval processing of the associated metadata field 525 in a subsequent decompression step.

Symmetric Decryption

For each encrypted PosCigar string information 515 field in a row, the decryption module 620 derives the SE decryption key $K_{sc}$ from the patient master key $K_m$ and applies symmetric decryption using said key $K_{sc}$ and the random salt $R_i$ associated with the $i^{th}$ encrypted data block 515 to generate the decrypted reference-based information block 510.

Decompression

In accordance with the actual encoding embodiment, the decompression module 630 may apply a first step of entropy decoding (for instance VLC decoding) to decode the reference-based compressed position data block 510, then a second step of differential decoding to decode the position-based raw alignment data.

The decompression module 630 also retrieves the metadata information block 525 from the partial data retrieval module 610 and decodes said metadata information block 525 in accordance with the encoding embodiment, for instance with the gunzip reverse algorithm for a gzip encoding embodiment. The decompression module concatenates the decrypted position information 500, the decrypted position-based raw alignment information and the decompressed metadata information to reconstruct the raw alignment data in the position-based format as represented by FIG. 3.

Reverse Transposition

As illustrated by FIG. 2a and FIG. 2b, the conversion between the position-based and the read-based formats is equivalent to a matrix transposition, with the index of the reads as one dimension and the position of the reference genome as the other dimension. The transposition operation is fully reversible so the position-based format can be inversely transposed into a read-based format such as SAM, BAM or CRAM if necessary in the bioinformatics workflow, for instance to display reads overlapping a region of interest with a viewer. FIG. 7 shows a pseudo-code algorithm that may be used to integrally reconstruct a read-based data structure from the proposed position-based data structure.

Experimental Results

Figure 8:
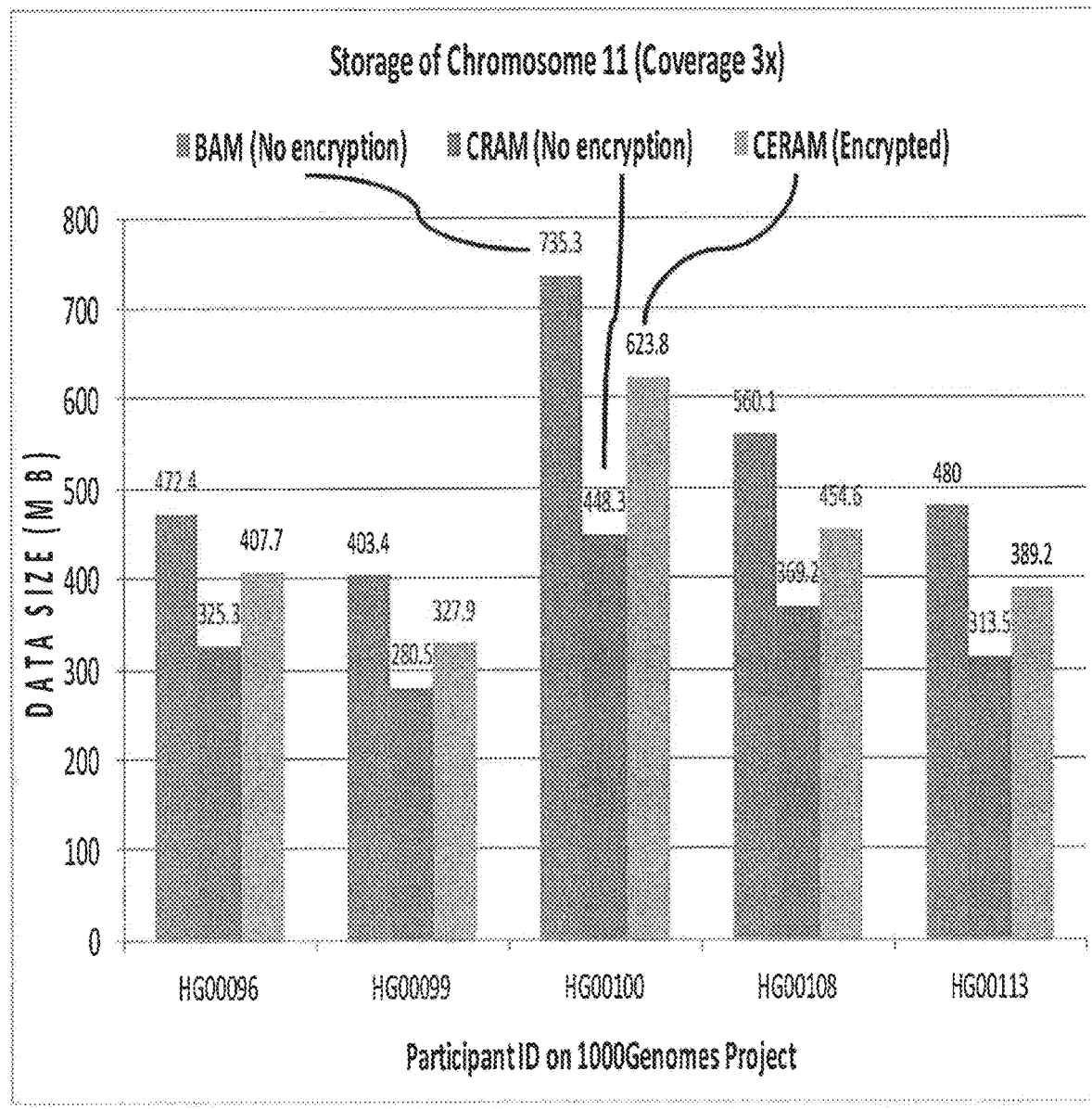
FIG. 8 illustrates some experimental results regarding the storage efficiency for a possible embodiment of the proposed methods and systems.

The proposed methods and systems provide several improvements over the prior art methods which only address either the storage efficiency, or the privacy enforcement requirements. FIG. 8 compares the average storage costs on several randomly selected real data files that are taken from the 1000 Genomes Project repository (ftp://ftp.1000genomes.ebi.ac.uk/vol1/ftp/phase3/data/) for respectively the de facto standard BAM genomic alignment binary format, the commonly used clear compressed genomic alignment file format CRAM, and the proposed compressed encrypted file format SECRAM. By directly combining an order-preserving encryption scheme with a reference-based data compression scheme in SECRAM, it is possible to improve the storage efficiency by 18% in average compared to the BAM format without excess encryption overhead compared to CRAM (34% compression efficiency over BAM, but no privacy or security features).

Figure 9A:
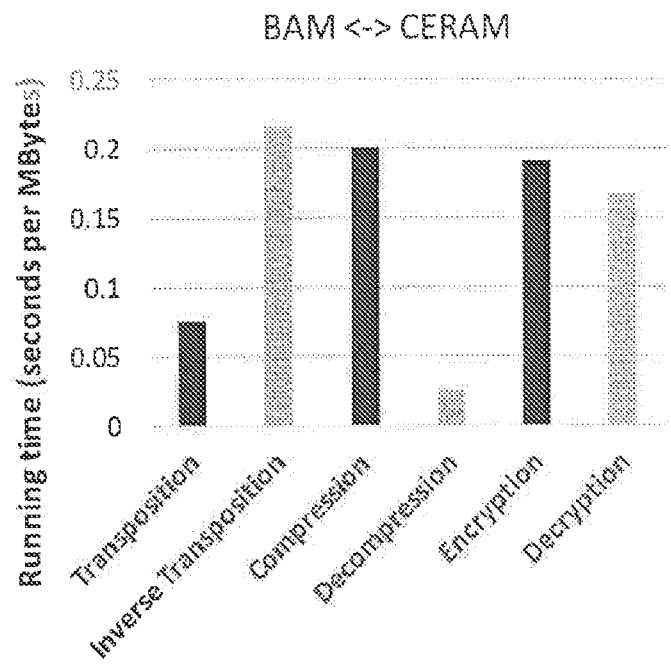
FIGS. 9A and 9B illustrate some experimental results regarding the computational efficiency for a possible embodiment of the proposed methods and systems.

The proposed method also enables faster genomic data queries compared to state of the art methods as the queries related to one position are more efficient than those related to a complete read. Examples of queries of one position include the coverage of a position, the variants (substitution, insertion and deletion) and quality scores. The complexity of answering these queries is $O(C)$, where C is the coverage of this position. The overall complexity of iterating all positions in the range $[P_1,P_2]$ is $O((P_2-P_1)C)$. FIG. 9a) shows the average conversion time between BAM and SECRAM on real genomic datasets, in a possible embodiment of the genomic data encoder 100 (resp. the genomic data decoder 600) running with a single thread on a commodity computing machine. The black bars show the three steps of conversion from BAM to SECRAM (transposition, compression, encryption) by the genomic data encoder 100 whereas the light gray bars show the three steps of conversion from SECRAM to BAM (decryption, decompression, inverse transposition) by the genomic data decoder 600. Each step takes less than 0.25 seconds for 1 megabyte of data.

Figure 9B:
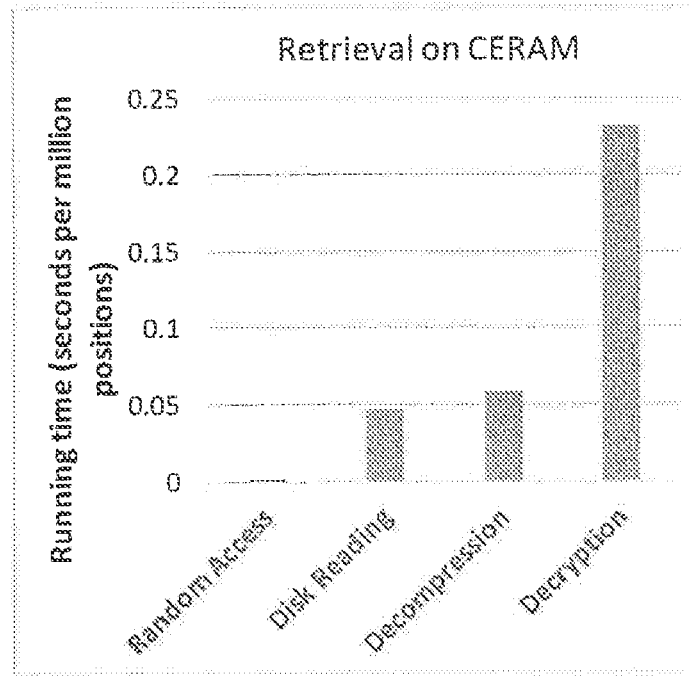

As will be apparent to those skilled in the art of computer processing optimization, a further possible improvement may consist in parallelizing the conversion steps for instance by splitting the BAM file in different chromosome references and processing each BAM to SECRAM conversion on a parallel thread for each chromosome. FIG. 9b) shows the average runtime cost of a possible embodiment of the genomic data decoder 600 to retrieve, decompress and decrypt a SECRAM genomic data sample in a range of 1 million positions. The real data size of 1 million positions depends on the coverage. In the experiment of FIG. 9b), real datasets of coverage about 3× were used, resulting in a real data size of slightly more than 1 megabyte. This experiment demonstrates the efficiency of the order-preserving encryption data retrieval stage while the decryption step causes the main runtime overhead in the overall genomic data decoder processing time.

OTHER EMBODIMENTS AND APPLICATIONS

As will be apparent to those skilled in the art of computer processing optimization, a further possible improvement may also consist in parallelizing certain steps of the methods, and/or adapting them to certain specific hardware processor units.

As will be apparent to those skilled in the art of genomic data compression, in another possible improvement, a lossy compression scheme such as those listed on the CRAM toolkit (http://www.cbi.ac.uk/ena/software/cram-toolkit) or the Quartz scheme may be applied as a pre-processing step prior to genomic data encoding to remove read names and/or to reduce the precision of the quality scores without significantly impacting the read-based alignment data information prior to transposition, compression and encryption.

As will be apparent to those skilled in the art of digital data communications, the methods described herein may be indifferently applied to various data structures such as data files or data streams. The terms "data", "data structures", "data fields", "file", or "stream" may thus be used indifferently throughout this specification.

Although the detailed description above contains many specific details, these should not be construed as limiting the scope of the embodiments but as merely providing illustrations of some of several embodiments.

While various embodiments have been described above, it should be understood that they have been presented by way of example and not limitation. It will be apparent to persons skilled in the relevant art(s) that various changes in form and detail can be made therein without departing from the spirit and scope. In fact, after reading the above description, it will be apparent to one skilled in the relevant art(s) how to implement alternative embodiments.

In addition, it should be understood that any figures which highlight the functionality and advantages are presented for example purposes only. The disclosed methods are sufficiently flexible and configurable such that they may be utilized in ways other than that shown.

Although the term "at least one" may often be used in the specification, claims and drawings, the terms "a", "an", "the", "said", etc. also signify "at least one" or "the at least one" in the specification, claims and drawings.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Certain embodiments are described herein as including logic or a number of components, modules, or mechanisms. Modules may constitute either software modules (e.g., code embodied on a machine-readable medium or in a transmission signal) or hardware modules. A "hardware module" is a tangible unit capable of performing certain operations and may be configured or arranged in a certain physical manner. In various example embodiments, one or more computer systems (e.g., a standalone computer system, a client computer system, or a server computer system) or one or more hardware modules of a computer system (e.g., a processor or a group of processors) may be configured by software (e.g., an application or application portion) as a hardware module that operates to perform certain operations as described herein.

In some embodiments, a hardware module may be implemented mechanically, electronically, or any suitable combination thereof. For example, a hardware module may include dedicated circuitry or logic that is permanently configured to perform certain operations. For example, a hardware module may be a special-purpose processor, such as a field-programmable gate array (FPGA) or an ASIC. A hardware module may also include programmable logic or circuitry that is temporarily configured by software to perform certain operations. For example, a hardware module may include software encompassed within a general-purpose processor or other programmable processor. It will be appreciated that the decision to implement a hardware module mechanically, in dedicated and permanently configured circuitry, or in temporarily configured circuitry (e.g., configured by software) may be driven by cost and time considerations.

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions described herein. As used herein, "processor-implemented module" refers to a hardware module implemented using one or more processors.

Similarly, the methods described herein may be at least partially processor-implemented, a processor being an example of hardware. For example, at least some of the operations of a method may be performed by one or more processors or processor-implemented modules.

Some portions of the subject matter discussed herein may be presented in terms of algorithms or symbolic representations of operations on data stored as bits or binary digital signals within a machine memory (e.g., a computer memory). Such algorithms or symbolic representations are examples of techniques used by those of ordinary skill in the data processing arts to convey the substance of their work to others skilled in the art. As used herein, an "algorithm" is a self-consistent sequence of operations or similar processing leading to a desired result. In this context, algorithms and operations involve physical manipulation of physical quantities.

Although an overview of the inventive subject matter has been described with reference to specific example embodiments, various modifications and changes may be made to these embodiments without departing from the broader spirit and scope of embodiments of the present invention. For example, various embodiments or features thereof may be mixed and matched or made optional by a person of ordinary skill in the art. Such embodiments of the inventive subject matter may be referred to herein, individually or collectively, by the term "invention" merely for convenience and without intending to voluntarily limit the scope of this application to any single invention or inventive concept if more than one is, in fact, disclosed.

The embodiments illustrated herein are believed to be described in sufficient detail to enable those skilled in the art to practice the teachings disclosed. Other embodiments may be used and derived therefrom, such that structural and logical substitutions and changes may be made without departing from the scope of this disclosure. The Detailed Description, therefore, is not to be taken in a limiting sense, and the scope of various embodiments is defined only by the appended claims, along with the full range of equivalents to which such claims are entitled.

Moreover, plural instances may be provided for resources, operations, or structures described herein as a single instance. Additionally, boundaries between various resources, operations, modules, engines, and data stores are somewhat arbitrary, and particular operations are illustrated in a context of specific illustrative configurations. Other allocations of functionality are envisioned and may fall within a scope of various embodiments of the present invention. In general, structures and functionality presented as separate resources in the example configurations may be implemented as a combined structure or resource. Similarly, structures and functionality presented as a single resource may be implemented as separate resources. These and other variations, modifications, additions, and improvements fall within a scope of embodiments of the present invention as represented by the appended claims. The specification and drawings are, accordingly, to be regarded in an illustrative rather than a restrictive sense.

Finally, it is the applicant's intent that only claims that include the express language "means for" or "step for" be interpreted under 35 U.S.C. 112, paragraph 6. Claims that do not expressly include the phrase "means for" or "step for" are not to be interpreted under 35 U.S.C. 112, paragraph 6.

What is claimed is:

1. A method to encode genomic data alignment information organized as a read-based alignment information data stream, comprising:
    Transposing, with a processor, the read-based alignment information data stream into a position-based alignment information data stream,
    wherein a character is a start marker for each short read in the position-based alignment information data stream, the start marker followed by metadata information regarding at least a nucleotide base identified at a position with an associated quality score;
    Encoding, with a processor, the position-based alignment information data stream into a reference-based compressed position data stream; and
    Encrypting, with a processor, the reference-based compressed position data stream into a compressed encrypted alignment data stream, including independently encrypting variant information for each row of a data structure in a storage that stores the compressed encrypted alignment data stream, providing privacy control of specific compressed encrypted alignment data within the stored compressed encrypted alignment data stream, the encrypting the reference-based compressed position data stream into a compressed encrypted alignment data stream comprising, first, an order-preserving encryption scheme, and second, encrypting sensitive information at each position,
    wherein the method results in increased storage efficiency or faster genomic data queries.

2. The method of claim 1,
    wherein encoding the position-based alignment information data stream into a reference-based compressed position data stream comprises differential encoding.

3. The method of claim 2,
    wherein differential encoding comprises recording, for each position in the reference-based compressed position data stream, the alignment differences relative to the alignment reference sequence, and
    wherein only the differences for each position with respect to the reference-based compressed position data stream are recorded.

4. The method of claim 1,
    wherein encoding the position-based alignment information data stream into a reference-based compressed position data file further comprises entropy coding.

5. The method of claim 1,
    wherein the order preserving encryption scheme is configured to retrieve resulting encrypted data for each row of the data structure without decrypting a whole block data.

6. The method of claim 1,
wherein encrypting the reference-based compression position data stream into a compressed encrypted alignment data stream comprises encrypting the position-based alignment information with a symmetric encryption scheme.

7. The method of claim 6,
wherein the symmetric encryption scheme is a stream cipher.

8. The method of claim 7,
wherein the symmetric encryption scheme is a block cipher operating in a stream cipher mode.

9. A method to retrieve genomic data alignment information from a compressed encrypted alignment data stream, recorded on a storage, comprising:
Receiving a genomic alignment range query [Pos1, Pos2] from a genomic data analysis system;
Retrieving from the storage, with a processor, the subset of the compressed encrypted alignment data stream corresponding to the genomic alignment range [Pos1, Pos2] in the compressed encrypted alignment data stream;
Decrypting, with a processor, the compressed encrypted alignment data stream into a reference-based compressed position data stream corresponding to the genomic alignment range [Pos1, Pos2], including independently decrypting variant information for each row of a data structure in the storage that stores the compressed encrypted alignment data stream, providing privacy control of specific compressed encrypted alignment data within the stored compressed encrypted alignment data stream; and
Decoding, with a processor, the reference-based compressed position data stream into a position-based alignment information data stream corresponding to the genomic alignment range [Pos1, Pos2],
wherein the method results in increased storage efficiency or faster genomic data queries, and
wherein decoding the reference-based compressed position data stream comprises retrieving a metadata information block and decoding the metadata information block in accordance with an encoding embodiment.

10. The method of claim 9, further comprising:
reverse transposing, with a processor, the position-based alignment information data stream into a read-based alignment information data,
wherein a character is a start marker for each short read in the portion-based alignment information data stream, the start marker followed by metadata information regarding at least a nucleotide base identified at a position with an associated quality score.

11. The method of claim 9,
wherein retrieving the subset of the compressed encrypted alignment data stream for the genomic alignment range [Pos1, Pos2] comprises retrieving the symmetric encrypted data and the metadata stored in data blocks between the order-preserving encrypted position associated with Pos1 and the order-preserving encrypted position associated with Pos2.

12. The method of claim 11,
wherein decrypting the compressed encrypted alignment data stream into a reference-based compressed position data stream corresponding to the genomic alignment range [Pos1, Pos2] comprises symmetric decryption of the symmetric encrypted data between the order-preserving encrypted position associated with Pos1 and the order-preserving encrypted position associated with Pos2.

13. The method of claim 12,
wherein the symmetric decryption scheme is a stream decipher.

14. The method of claim 12,
wherein the symmetric decryption scheme is a block decipher operating in a stream decipher mode.

15. The method of claim 9,
wherein decoding the position-based alignment information data stream into reference-based compressed position data stream comprises entropy decoding.

16. The method of claim 9,
wherein decoding the position-based alignment information data stream into reference-based compressed position data stream comprises differential decoding.

17. The method of claim 1,
wherein encoding the position-based alignment information data stream into a reference-based compressed position data file further comprises text coding algorithms, and
wherein the reference-based compressed position data file is a compact binary reference-based compressed position data file.

18. The method of claim 1,
wherein encoding the position-based alignment information data stream into a reference-based compressed position data file further comprises variable length coding,
wherein the variable length coding is configured to compress differences found in reference-based compression, and
wherein the variable length coding is configured to compress differences found in mapping quality scores.

19. The method of claim 15,
wherein the entropy decoding is VLC decoding.

20. The method of claim 9,
wherein the encoding embodiment is a gunzip reverse algorithm, and
wherein decoding comprises concatenating the reference-based compressed position data stream, the position-based alignment information data stream, and the metadata information block to reconstruct the genomic data alignment information.

* * * * *